US00PP07914P

United States Patent [19]

Marciel

[11] Patent Number: Plant 7,914

[45] Date of Patent: Jul. 21, 1992

[54] MINIATURE ROSE PLANT NAMED DEVORO

[75] Inventor: Stanley G. Marciel, Aptos, Calif.

[73] Assignee: DeVor Nurseries, Inc., Watsonville, Calif.

[21] Appl. No.: 627,038

[22] Filed: Dec. 13, 1990

[51] Int. Cl.[5] ..... A01H 5/00
[52] U.S. Cl. ..... Plt./7.1
[58] Field of Search ..... Plt. 7, 7.1, 10.1

[56] References Cited

U.S. PATENT DOCUMENTS

P.P. 6,506 1/1989 Saville ..... Plt. 7
P.P. 6,559 1/1989 Jolly ..... Plt. 7

*Primary Examiner*—Howard J. Locker
*Attorney, Agent, or Firm*—Christie, Parker & Hale

[57] ABSTRACT

A new miniature rose plant producing orange red and yellow blend flowers.

1 Drawing Sheet

SUMMARY OF THE INVENTION

The present invention relates to a new and distinct variety of rose plant of the miniature rose class, which was originated by my crossing as seed parent the variety known as 'Amber Flash', (U.S. Plant Pat. No. 5,271) and as pollen parent the variety known as 'Rhumba' (U.S. Plant Pat. No. 1,919). The varietal denomination of this new rose is 'Devoro'.

Among the novel characteristics possessed by this new variety which primarily distinguishes it from its parents and all other varieties of which I am aware are its unusual orange red and yellow blend flowers. Flowers open well upon aging and the new variety is especially suited for growing as a pot rose and as patio tree roses.

Asexual reproduction by propagation by rooting cuttings of the new variety, as performed in Pleasanton, Calif. and Watsonville, Calif., shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Color Chart (RHSCC). The terminology used in color description herein refers to plate numbers in the aforementioned color chart.

Parentage: Seedling.
*Seed parent.*—'Amber Flash'.
*Pollen parent.*—'Rhumba'.
Class: Miniature.

The following observations are made of specimens grown under glass in Watsonville, Calif.

FLOWER

Blooming habit: Continuous.

A. Bud:
(1) *Size.*—Medium for miniature.
(2) *Form.*—Ovoid.
(3) *Color.*—As sepals divide, bud coloration exhibits a range of orange red and yellow hues. Color of petals undersurface of first opened outer petals appears as near 34A-B to 35A but petal undersurface of some outer petals are yellow orange, near 20B. When sepals fall fully to horizontal, bud coloring appears more orange red and yellow near 20B to 21D infused with red washing, near 42A to 42B, with red coloring primarily at petal undersurface margins and washing into the petal below the margin.
(4) *Sepals.*—Longer than bud, lightly foliated.
(5) *Peduncle.*—Length — about 1.9 to 2.0 cm with small prickles. Aspect — near straight. Strength — erect, slender. Color — medium green.
(6) *Calyx.*—Smooth, pear-shaped, does not split; 0.7 cm×0.6 cm.

B. Bloom:
(1) *Size.*—Average size when fully expanded — about 5.5 cm; depth 1.5 to 2 cm.
(2) *Borne.*—Usually singly.
(3) *Form.*—Cupped at first, becoming flat; petals somewhat lobed; outer petals quill to points, especially as blooms age.
(4) *Petalage.*—Under normal conditions average is about 17.
(5) *Color.*—After sepals fall and petals begin to unfurl, flower coloring appears as near 29A to 28A, with deeper tonality at petal apices and in some veining on petals. Individual petals show blend of orange red, near 42A to 42B, and yellow, near 21D, merging at about ⅓ from petal margin. Petal undersurface remains near 19A to 19C. As blooms age, orange red coloration reddens to near 35A to C on inner petals which become more visible in the fully open stage. General tonality before flowers age is attractive orange to orange red. Color of petal at point of attachment is near 12A. Petaloids number 1 to 3 and are generally near 23B with near 12C at the margin of the base and near 12A as the base color and, when present, are visible in open blooms.

(6) *Lasting quality.*—Long lasting on the plant and after cutting.

C. Petals:

(1) *Texture.*—Semi-leathery.

(2) *Appearance.*—Inside velvety and outside satiny.

(3) *Form.*—Broad, fan shaped with pointed apices.

(4) *Arrangement.*—Regularly arranged, imbricated.

(5) *Petaloids in center.*—Few.

(6) *Persistence.*—Persist.

(7) *Fragrance.*—Moderate musk.

REPRODUCTIVE ORGANS

A. Stamens, filaments and anthers:

*Arrangement and color.*—Stamens introrse, about 49-52; anthers about 0.2 cm, near 13C; filaments 0.3-0.5 cm, near 17C. Color of filaments is near 17A.

B. Pistils: About 62 to 65.

C. Pollen:

*Color.*—Near 21C.

D. Styles: Medium length, even; 0.8 to 0.9 cm, color is near 1D.

E. Stigmas:

*Color.*—Near 4A.

F. Hips: Round, color is near 31A at maturity.

PLANT

A. Form: Upright, compact.

B. Growth: Vigorous, free branching.

*Height attained.*—About 54 cm.

C. Foliage: Compound 3, 5 and 7 leaflets.

(1) *Size.*—Medium.

(2) *Quantity.*—Abundant.

(3) *Color.*—Upper side — near 147A. Under side — near 147B.

(4) *Shape.*—Oval, pointed, about 10 cm × 6.5 cm.

(5) *Texture.*—Upper side — semi-leathery. Under side — matte.

(6) *Edge.*—Serrate, (denticulate).

(7) *Serration.*—Ordinary.

(8) *Leaf stem.*—Color — medium green.

(9) *Stipules.*—Medium length, hair adnate.

(10) *Rachis.*—2.5 cm on 3 leaf; 5 cm on 5 leaf; 7 cm on 7 leaf.

(11) *Petioles.*—Length — 0.5 on 3 leaf; 1.5 cm on 5 and 7 leaf.

(12) *Ribs and veins.*—Slightly depressed on top, rounded underneath. Rachis: Small spines underneath.

(13) *Resistance to disease.*—Moderate resistance to mildew, blackspot and rust.

D. Wood:

*Color.*—Medium green.

*Bark.*—Smooth.

E. Thorns:

*Quantity (main stalk).*—Ordinary.

*Form.*—Pointed, thin, declining.

*Length.*—About 0.6 cm.

*Color.*—Near 165A with near 144A at top and base.

*Position.*—Irregular.

*Prickles.*—Few.

F. Winter hardiness: Needs protection in severe climates.

I claim:

1. A new and distinct variety of rose plant of the miniature rose class, substantially as shown and described.

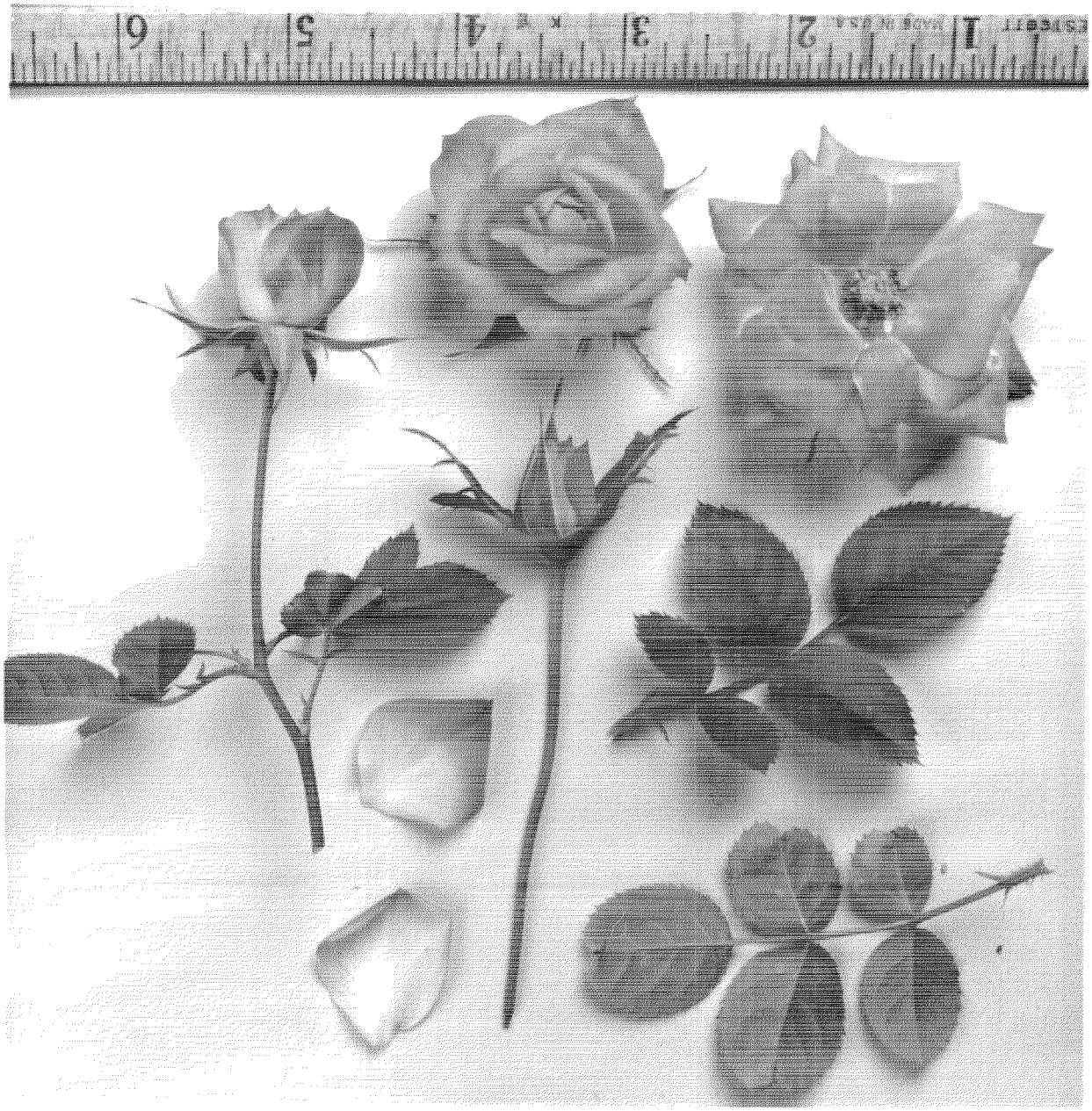

* * * * *